United States Patent
Keitel et al.

(10) Patent No.: US 6,216,690 B1
(45) Date of Patent: Apr. 17, 2001

(54) METHOD AND APPARATUS FOR RAPID CONTROL OF SET INSPIRED GAS CONCENTRATION IN ANESTHESIA DELIVERY SYSTEMS

(75) Inventors: Todd A. Keitel, DeForest; Robert Q. Tham, Middleton, both of WI (US)

(73) Assignee: Datex-Ohmeda, Inc., Madison, WI (US)

( * ) Notice: Subject to any disclaimer, the term of this patent is extended or adjusted under 35 U.S.C. 154(b) by 0 days.

(21) Appl. No.: 09/170,168

(22) Filed: Oct. 13, 1998

Related U.S. Application Data
(60) Provisional application No. 60/062,857, filed on Oct. 15, 1997.

(51) Int. Cl.⁷ .................................................. A61M 15/00
(52) U.S. Cl. .............................. 128/203.12; 128/204.21; 128/204.13
(58) Field of Search ................... 128/203.12, 204.21, 128/204.23, 204.18, 204.13, 203.25

(56) References Cited

U.S. PATENT DOCUMENTS

| | | | |
|---|---|---|---|
| 4,127,121 | 11/1978 | Westenskow et al. | 128/142 R |
| 4,215,409 | 7/1980 | Strowe | 364/510 |
| 4,345,612 | 8/1982 | Koni et al. | 137/101.19 |
| 4,406,302 | 9/1983 | Olesen | 137/514.5 |
| 4,702,241 | 10/1987 | Gravenstein et al. | 128/204.25 |
| 5,094,235 | 3/1992 | Westenskow et al. | 128/204.22 |
| 5,237,990 * | 8/1993 | Psaros et al. | 128/204.21 |
| 5,265,594 * | 11/1993 | Olsson et al. | 128/204.18 |
| 5,320,093 | 6/1994 | Raemer | 128/203.12 |
| 5,400,778 | 3/1995 | Jonson et al. | 128/205.19 |
| 5,509,406 | 4/1996 | Kock et al. | 128/203.14 |
| 5,546,931 | 8/1996 | Rusz | 128/203.12 |
| 5,619,986 | 4/1997 | Werner et al. | 128/204.21 |
| 5,673,688 | 10/1997 | Tham et al. | |
| 5,699,788 * | 12/1997 | Lekholm et al. | 128/203.12 |
| 5,771,882 * | 6/1998 | Psaros et al. | 128/203.12 |
| 5,806,513 * | 9/1998 | Tham et al. | 128/204.22 |

FOREIGN PATENT DOCUMENTS

| | | |
|---|---|---|
| 397 011 | 11/1990 | (EP) . |
| 894 506 | 2/1999 | (EP) . |

OTHER PUBLICATIONS

Ehrenwerth M.D., Jan and Eisenkraft M.D., James B., *Anethesia Equipment*, Chapter 33, pp. 685–691, 1993.
Phillips, Charles L. and Nagle Jr., H. Troy, *Digital Control System Analysis and Design*, p. 254, 1984.
Clarke, D.W., *Advances in Model–Based Predictive Control*, pp. 3–21, 1994.
*Adaptive Control of Closed–Circuit Anesthesia*—R. Vishnoi et al., IEEE Transactions on Biomedical Engineering, US, IEEE, Inc., New York, vol. 38, No. 1, pp. 39–46, XP000225246, ISSN: 0018–9294.

\* cited by examiner

*Primary Examiner*—John G. Weiss
*Assistant Examiner*—V. Srivastava
(74) *Attorney, Agent, or Firm*—Andrus, Sceales, Starke & Sawall, LLP (57) ABSTRACT

A method and system for rapid control of set inspired gas concentration is disclosed for operating a medical anesthesia delivery system and for controlling the flow and concentration of gases and anesthesia vapor delivered to a patient. Control of the inspired gas and agent concentration is accomplished by operating in different control priority modes. In a flow priority control mode, the user may set, either directly or indirectly, the total fresh gas flow rate. The total fresh gas flow rate can then be slowly be varied by the control algorithm, while the vaporizer concentration is actively controlled to achieve the user set inspired gas concentration. The invention includes a process for switching from the flow priority control mode into a concentration priority mode for low flow rates. By throttling the flow, the patient will receive nearly an instantaneous change in the amount of agent and fresh gas without having the transport delay associated with a change in the agent concentration. Sensors are used to monitor agent concentration and minute volume, and a processor is programmed to estimate the concentration of the agent in the pipeline to select the control priority mode, and control the agent vaporizer and the fresh gas flow controller to selectively switch between control priority modes and operate extremely efficiently while in the concentration priority mode by changing the flow rate instead of the agent concentration.

25 Claims, 8 Drawing Sheets

METHOD AND APPARATUS FOR RAPID CONTROL OF SET INSPIRED GAS CONCENTRATION IN ANESTHESIA DELIVERY SYSTEMS

CROSS REFERENCE TO RELATED APPLICATION

This application claims the priority of U.S. provisional patent application, Appln. No. 60/062,857, filed Oct. 15, 1997.

BACKGROUND OF THE INVENTION

The present invention relates generally to medical anesthesia delivery machines, and more particularly, to a method and apparatus to provide rapid control of set inspired gas concentration in circular type anesthesia breathing circuits for providing breathing gases and anesthesia to a patient.

Fundamentally, medical anesthesia delivery systems regulate the flow and mixture of breathing gases inspired and expired by a patient undergoing treatment. Inspired breathing gases typically consist of a mixture of oxygen, nitrous oxide, air and other gases. Anesthesia is administered by clinicians, who command the anesthesia delivery system to control gas and anesthetic concentrations throughout the three phases of patient anesthesia—induction, maintenance and emergence. Each of these phases is characterized by different demands placed on the anesthesia delivery control system. For example, during induction, it is important that high fresh gas flow be supplied to the breathing circuit in order to provide a quick increase in the concentration of breathing gas and anesthesia agent required. At induction, patient uptake of nitrous oxide and volatile anesthesia agent is very high and precise control of the gas flow during this phase is relatively unimportant. On the other hand, during the maintenance and emergence phases, control of the fresh gas flow is more critical. In some practices, prior to emergence from anesthesia, flow of the anesthetic agent is discontinued, and minimal fresh gas flow is introduced into the breathing circuit to gradually recover the patient from anesthesia. After surgery is completed, fresh gas flows are increased to rapidly reduce the anesthetic agent concentration in the inspired mixture and to facilitate a "washout" of anesthetic agent from the patient's bloodstream. Accurate and dependable control of the concentration and flow of gas and anesthetic vapor is thus critical to the function of the anesthesia delivery system and to the safety of the patient undergoing anesthesia.

A typical anesthesia machine mixes the gases which constitute the fresh breathing gas mixture according to operator settings or instructions from a control system. Fresh breathing gas is then conveyed through a vaporizing unit which provides anesthetic vapor to the fresh gas. Fresh gas then enters a breathing circuit which circulates inspired gases to the patient through an inspiratory conduit. Expired gases are conveyed away from the patient via an expiratory conduit. A re-breathing conduit is typically provided to route expired gases from the expiratory conduit back to the inspiratory conduit and is provided with a carbon dioxide absorber for removing carbon dioxide from the re-breathed gas. A ventilator assembly is provided in communication with the breathing circuit as a reservoir for breathing gases and to provide the pressure force for ventilator-assisted inspiration and expiration in lieu of spontaneous breathing by the patient or manual bagging by the clinician. A pop-off valve is typically provided in conjunction with the ventilator to permit release of excess gas from the breathing circuit.

The advantages of low or minimal fresh gas flow rates into the breathing circuit have long been recognized. Minimal or low fresh gas flow offers the advantages of more efficient management and conservation of fresh gas and anesthetic agent, as well as patient-generated heat and humidity in the breathing gas. Additionally, the effects of leaks and changes in patient uptake are more pronounced, and thus more detectable, in low flow delivery schemes. This permits more careful monitoring of the therapy provided to the patient. Minimal or low fresh gas flow delivery schemes, however, have heretofore presented a number of problems which have resulted in reduced operator confidence.

The response time for low flow systems to reach steady state after a disturbance or change in user-set concentrations varies inversely with the flow rate of fresh gas, that is, changes occur faster with higher flow rates. Thus, a major problem with low or minimal flow delivery schemes, particularly in closed-circuit delivery methods, is that system response to changes in user-set gas and vapor concentrations is unsatisfactory. Low flow delivery schemes have been consequently less robust, more susceptible to instability, and more sensitive to disturbances, such as leaks and changes in patient uptake, than higher flow delivery schemes. As a result, clinicians who are accustomed to manually adjusting fresh gas flows according to their own judgment to compensate for or negate the effects of leakage have low confidence in the safety of low or minimal flow systems. Such systems do not allow for adequate clinician control of the fresh gas flow to the breathing circuit.

There have been attempts to reduce fresh gas flows by operating the breathing circuit in closed circuit fashion whereby fresh gas is added to the breathing circuit at the rate at which it is consumed by the patient. Closed-circuit delivery schemes require very precise measurement of the gas volumes in the breathing circuit in order to maintain adequate control thereon. This is a consequence of the fact that the volume of fresh gas that may be used to replenish the breathing circuit, and thus adjust the gas volumes, is limited to the volume lost from the breathing circuit due to patient uptake and, often, leakage. Control techniques for closed-circuit delivery schemes are extremely sensitive to loss in circuit gases through leaks or changes in patient gas exchange. This increases the safety risks associated with the replenishment of the circuit gas volume and maintenance of the ventilatory tidal volume.

Attempts to address the slow response times of closed-circuit delivery systems have done so primarily at the expense of inefficient management of fresh gas flow. An example of such a prior art device uses a control system which enables closed-circuit anesthesia delivery systems to quickly respond to changes in user set points. Feedback loops are utilized to control the concentrations of oxygen, carbon dioxide and anesthetic agent concentrations in the breathing circuit based on sensed values. These normally closed control loops may be opened and fresh gas flow increased for a predetermined time in response to a change in the desired user-set concentration for anesthetic agent or gas concentrations. Open-loop high flow operation has the effect of flushing the breathing circuit with fresh gas until the concentration of anesthetic approaches the new desired value. One disadvantage of such devices is that, once the control loop is closed and fresh gas flow reduced after the new set point has been reached, the system is sluggish in responding to and correcting disturbances in the breathing circuit gas concentrations.

There is thus desired an anesthesia delivery system that solves the aforementioned problems and permits clinicians to control the minimum amount of total fresh gas flow into the breathing circuit according to their own judgement and the clinical need. This provides increased user confidence in the anesthesia delivery system.

There is also desired an anesthesia delivery system control system which permits satisfactory anesthesia delivery system response during low or minimal flow of fresh gas and which is capable of conserving the amount of patient gases exhausted from the breathing circuit.

Therefore, it would be desirable to have an anesthesia delivery system control that can provide automatic control of gas and agent concentrations at low or minimal fresh gas flows and throughout variations in the rate of fresh gas flow. It would also be desirable to have an anesthesia delivery system that allows clinicians to set a minimum fresh gas flow to the breathing circuit. It would further be advantageous for an anesthesia delivery system to operate in a number of different modes, each based on a parameter priority capable of automatically switching between control priority modes based on a target fresh gas flow rate. It would therefore be extremely desirable to have a control for an anesthesia delivery system capable of performing each of the above described advantages that solves the aforementioned problems.

SUMMARY OF THE INVENTION

The present invention provides a method and apparatus for rapid control of set inspired gas concentration for operating a medical anesthesia delivery system and for controlling the flow and concentration of breathing gases and anesthesia vapor delivered to a patient that overcomes the aforementioned problems.

In accordance with one aspect of the invention, a medical anesthesia delivery system for administering respiration and anesthesia to a patient is disclosed having a gas supply, including a gas flow controller, to provide fresh breathing gas, and an anesthetic agent supply, including an agent vaporizer, in fluid communication with the gas supply to provide anesthetic agent into the fresh breathing gas. The gas flow controller and the agent vaporizer are each in fluid communication with a breathing circuit having a portion comprised substantially of inelastic components such that a volume displacement at a supply end will cause rapid volume displacement at a patient end. The supply end of the breathing circuit is connected to the gas supply and the anesthetic agent supply to deliver a mixture of fresh breathing gas and anesthetic agent to a patient at the patient end of the breathing circuit. The system includes at least one sensor connected in the breathing circuit to monitor a parameter of the fresh breathing gas and anesthetic agent, preferably minute volume and/or agent concentration. The medical anesthesia delivery system of the present invention also includes a system control connected to the gas flow controller, the agent vaporizer, the sensor, and a user interface. The system control receives signals from the sensor indicative of the measured parameter of the breathing gas and anesthetic agent and provides output control signals to the gas flow controller and the agent vaporizer. The user interface allows the entry of a user desired inspired agent concentration setting, and other relevant parameters. The control system has active feedback and feedforward control loops to create control signals capable of rapidly changing fresh breathing gas and anesthetic agent mixture flow rate, and therefore change anesthetic agent volume delivered to the patient connected to the patient end of the breathing circuit. By creating and sending gain weighted control signals to the gas flow controller and the agent vaporizer to change flow rate at the supply end of the breathing circuit, the present invention can make more efficient use of agent.

In accordance with another aspect of the invention, a method of controlling an anesthesia delivery system is disclosed having the steps of providing fresh breathing gases from a gas supply into a breathing circuit and providing an anesthesia agent into the fresh breathing gases in the breathing circuit for delivery of the fresh breathing gases and the anesthetic agent as a mixture to the patient. The method also includes sensing at least one parameter of the mixture in the breathing circuit and predicting a second parameter of the mixture indicative of a quality of the mixture as the mixture is about to enter the patient. The method next includes the step of controlling a flow rate of the mixture as the mixture travels through the breathing circuit to the patient so that the patient receives a desired amount of anesthesia agent based primarily on the controlled flow rate.

In accordance with yet another aspect of the invention, a control system is disclosed for use in an anesthesia delivery system having a user interface to input desired anesthesia agent parameters into the control system. A sensor is located in a delivery system to measure characteristics of the anesthesia agent and breathing gases. A processor is connected to the anesthesia delivery system, the user interface, and the sensor. The processor in this system is programmed to receive the desired anesthesia agent parameters from the user interface and the measured characteristics of the anesthesia agent and breathing gases from the sensor and estimate or measure an anesthesia agent concentration in the anesthesia delivery system. The processor is further programmed to selectively switch operation between two operating modes based on measured characteristics of the breathing gas and anesthetic agent. One of the operating modes provides control priority to agent concentration by changing a total fresh gas flow rate to achieve a desired inspiratory concentration setting. Another operating mode provides control priority to flow rate by changing agent concentration to achieve the desired inspiratory concentration setting. The control processor is also programmed to produce control signals receivable by the anesthesia delivery system in response to the selected M operating mode. The control signals being deliverable to the anesthesia delivery system to monitor and control flow rate of the anesthesia agent and the breathing gas in the breathing system to adjust the amount of anesthesia agent to a patient while in a concentration priority mode.

In accordance with yet another aspect of the invention, a control system for an anesthesia delivery system is disclosed having a user interface to input desired anesthesia agent parameters to the control system. A sensor is located in a delivery system to measure characteristics of the anesthesia agent and breathing gases. The control system includes an agent concentration computational module to estimate or measure agent concentrations in a breathing circuit to the patient and to estimate or measure the agent concentration in a re-breathing section of the breathing circuit. The control system also includes a control priority module section receiving input from the agent concentration computational module, the sensor, and the user interface to select one of two priority control modes and sets feedforward and feedback control priority gains. During low-flow allowable conditions, the control system can then deliver rapid changes in agent volume to the patient by rapidly changing the flow rate, while allowing direct intervention of agent concentration during high flow conditions.

In accordance with still another aspect of the invention, an improved control system for an anesthesia delivery system having an agent vaporizer in fluid communication with a gas flow controller connected to one end of the breathing circuit is disclosed in a system in which the breathing circuit has a re-breathing section to re-circulate at least a portion of an anesthetic agent and fresh gas mixture. The anesthesia delivery system also has sensors to measure minute volume and agent concentration in the breathing circuit. The improvement includes a processor control connected to receive signals from the sensors and output signals to the agent vaporizer and gas flow controller, wherein the processor is programmed to retrieve a fresh gas mixing characteristic behavioral parameter based upon characteristic of a particular anesthesia delivery system, and then estimate both anesthetic agent concentration into the breathing circuit and re-circulated anesthetic agent concentration through the re-breathing section of the breathing circuit. The controller next determines a flow rate of fresh gas, re-circulated gas, and anesthetic agent through the breathing circuit and chooses a priority mode of operation based on the flow rate determination. The processor control next determines control priority weighting gains and controls agent vaporizer output and gas flow controller output based on the weighting gains determination to maintain low anesthetic agent usage in low-flow conditions by increasing flow rate for rapid anesthetic agent volume change to the patient. The processor then adjusts anesthetic agent concentration at the agent vaporizer. Thereafter, the processor reduces the flow rate based on a prediction when the higher agent concentration will reach the patient through the breathing circuit.

While in the concentration priority mode, the system is extremely efficient in reducing the amount of agent and fresh gas by maintaining low flow rates while at the same time providing a way to avoid transport lag and provide nearly instantaneous response to changes in set inspired gas concentrations thereby reducing the amount of total anesthetic agent used.

While in the flow priority control mode, the user may set, either directly or indirectly, the total fresh gas flow rate when so desired, such as during induction masked cases, or uncuffed endotracheal tube cases, where high leakage is expected and therefore high flow rates are required.

The control scheme of the present invention significantly improves the performance of such anesthesia delivery systems. This approach to control of the anesthesia delivery system provides consistently rapid response to changes in set inspired gas concentrations, saves total anesthetic agent usage, and faithfully tracks the desired gas concentration settings. The following detailed description describes the preferred embodiment of the control scheme to achieve the priority control modes and the preferred embodiment to seamlessly blend the two control modes in one operating system.

Various other features, objects and advantages of the present invention will be made apparent from the following detailed description and the drawings.

BRIEF DESCRIPTION OF THE DRAWINGS

The drawings illustrate the best mode presently contemplated for carrying out the invention.

In the drawings.

DETAILED DESCRIPTION OF THE PREFERRED EMBODIMENT

Figure 1:
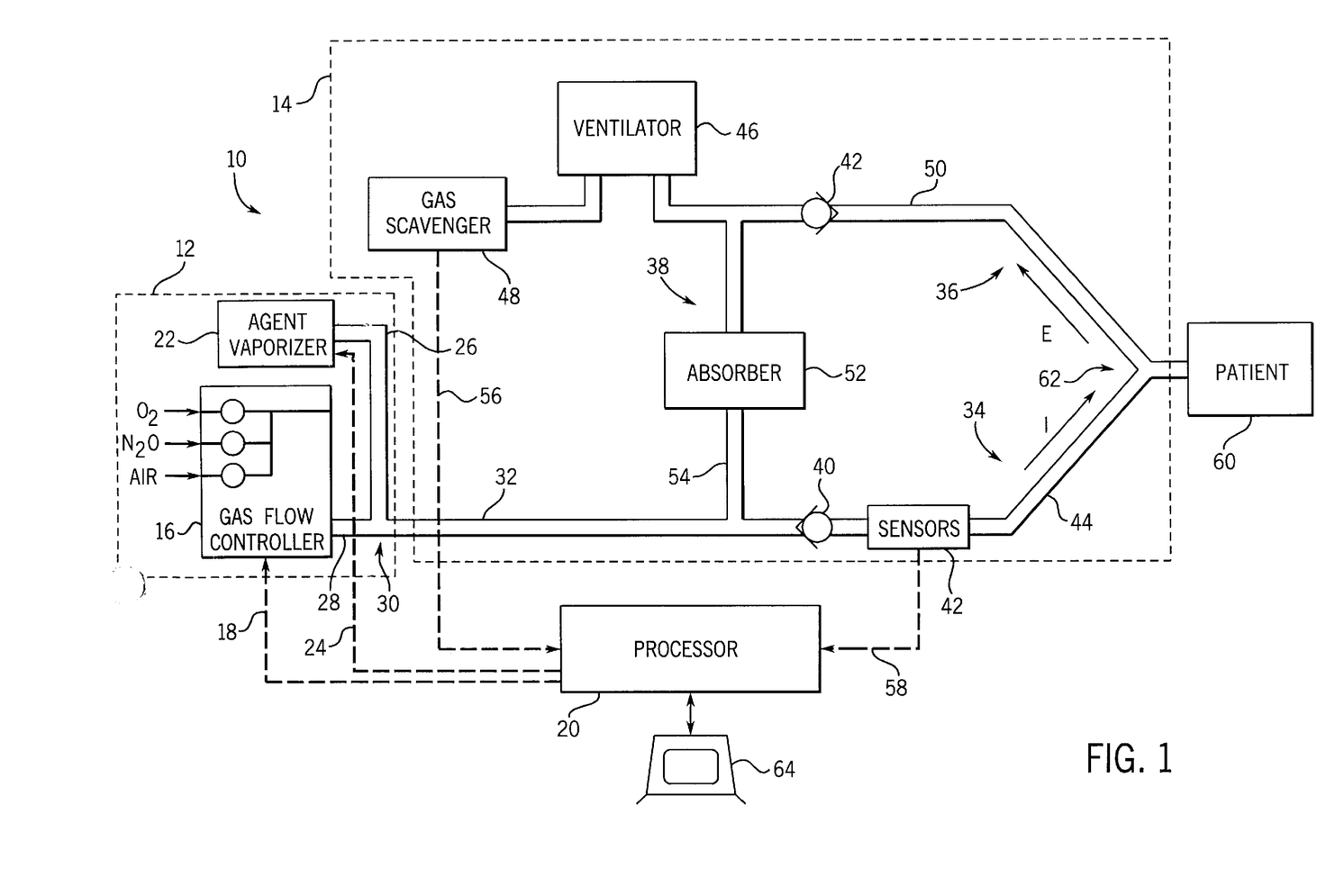
FIG. 1 is a schematic diagram of the elements of an anesthesia delivery system according to the present invention.

Referring to FIG. 1, an anesthesia delivery system 10 of a type suitable for practice of the present invention includes a fresh gas supply 12 which provides fresh gas to breathing circuit 14. Fresh gas supply 12 includes a source of oxygen $O_2$, nitrous oxide $N_2O$, air, or other gases as are conventionally used. The fresh gas supply 12 includes a gas flow controller 16 having a gas flow controller therein and receiving the oxygen, nitrous oxide, air, and/or other gases, and metering the component gases according to signals received on data bus 18 from processor 20. The fresh gas supply 12 also includes an agent vaporizer 22 which provides anesthetic vapor to the mixed gas from the gas flow controller 16 according to signals on data bus 24 from processor 20. Agent vaporizer 22 is connected to an outlet tube 26 which is in fluid communication with outlet tube 28 of gas flow controller 16 via a mixing tee 30 to output the mixed gas and anesthetic vapor mixture through inlet tube 32 in the breathing circuit 14.

Breathing circuit 14 includes an inspiratory section 34, and expiratory section 36, and a re-breathing section 38. The inspiratory section 34 includes check valve 40, sensors 42, and supply tubing 44. Expiratory section 36 includes check valve 42, ventilator 46, gas scavenger 48 and expiration tubing 50. The re-breathing section 38 includes a carbon dioxide absorber 52 in fluid communication with the inspiratory section 34 and the expiratory section 36 via re-breathing tubing 54. Gas scavenger 48 may optionally include a pop-off valve (not shown) to remove excess gases relieved from the breathing circuit and a pop-off flow sensor for generating a pop-off signal on line 56 to processor 20. Sensors 42 are connected to processor 20 via a data bus 58.

Breathing circuit 14 functions to deliver inspiratory gas to a patient 60 through inspiratory section 34 and remove expiratory gases from the patient through the expiratory section 36. Fresh gas enters breathing circuit 14 through inlet tube 32 and is conveyed to the patient 60 through the inspiratory section 34. Re-breathed gas is circulated through carbon dioxide absorber 52 in the re-breathing section 38 and mixed with the fresh gas from the inlet tube 32 prior to being inspired by patient 60. A Y-section 62 is provided to join the inspiratory section 34 and the expiratory section 36 for connection to the patient 60, as is well known. Under normal operating conditions, during inspiration, gas flows through inspiratory section 34 in the direction of arrow I with no flow in expiratory section 36. During expiration, gas flows through the expiratory section 36 in the direction of arrow E with no flow in inspiratory section 34. The inspiratory check valve 40 and the expiratory check valve 42 ensure unidirectional flow in the inspiratory section 36 and the expiratory section 34, respectively.

Fresh gas is provided from the fresh gas supply 12 to the breathing circuit 14 as dictated by the control system according to the present invention. As shown in the embodiment of FIG. 1, the control system is further embodied into processor 20 and is based upon inputs from the sensors 42 on data bus 58 and from user settings as input from the user interface 64. The user settings determine desired delivery parameters such as the inspired agent concentration. Sensors 42 include a circuit agent sensor for measuring agent concentration and a minute volume sensor for detecting minute volume through the inspiratory section 34. Each of the sensors provide signals on data bus 58 to processor 20 for controlling minute volume and agent concentration to patient 60, as will be described with reference to FIGS. 2–11.

It is noted that the measurement sensor may be located either in the inspiratory section 34, or alternatively, in the patient Y-piece 62. If the measurement sensor 42 is located in the Y-piece 62, the sensor must also differentiate between the inspired and expired agent concentration measurements.

Figure 2:
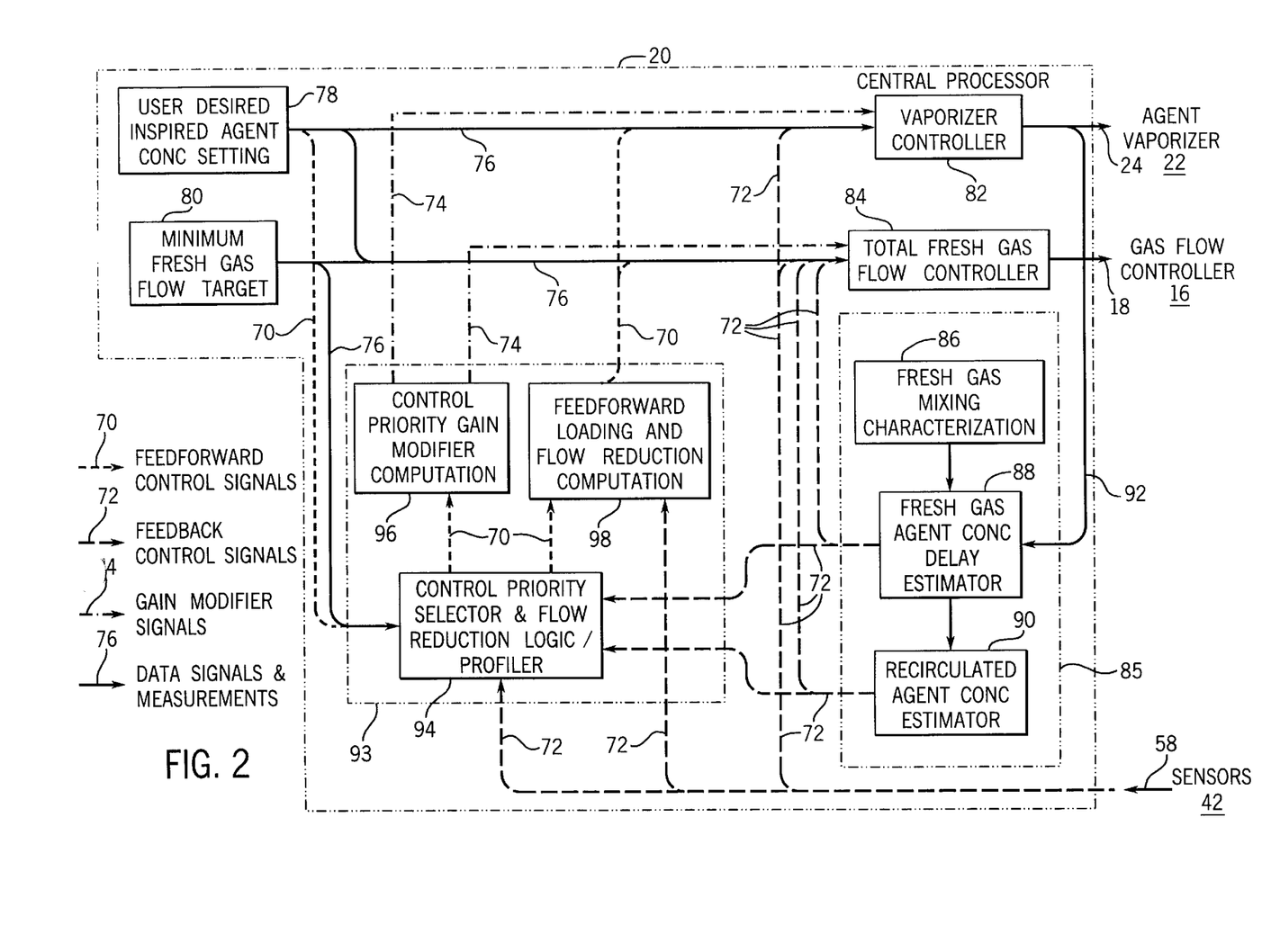
FIG. 2 is a functional block diagram of a portion of FIG. 1.

Referring to FIG. 2, a functional block diagram of the processor 20 is shown with a preferred signal flow pattern. Before proceeding to a detailed discussion of this control system, an overview of the system design concept will be described. Control of the inspired gas and agent concentration is accomplished by operating in different control priority modes. During a patient induction, where high leakage can be expected, such as in masked cases or uncuffed endotracheal tube cases, anesthesia delivery systems are optimally operated at high fresh gas flow to overcome the demands of gas uptakes and/or replenish large leaks. In these cases, it is preferable that the anesthesia delivery system operate in a flow priority control mode. In this mode, the user may set, either directly or indirectly, the total fresh gas flow rate. While operating in this mode, the total fresh gas flow may be varied slowly by the control algorithm of the present invention. Conversely, the vaporizer concentration is actively controlled to achieve the user set inspired gas concentration. However, in flow priority control mode, downstream responses to changes in vaporizer concentrations at the head, under low flow rate conditions, are unacceptable.

The present invention overcomes this problem by selectively switching to a concentration priority mode. When the operating mode provides priority to the agent concentration, the total fresh gas flow rate is actively changed to achieve the desired inspired concentration setting, as opposed to changing the vaporizer concentration setting. The theory behind the system is based on the well-known fact that in an inelastic vessel, gas volumes are displaced at the speed of sound. A change in the gas flow rate at the head of the flow path quickly alters the rate of the displacement of the gas at the end of the flow path. Referring back to FIG. 1, a change in the gas flow rate at the gas flow controller 16 will nearly instantly alter the rate of displacement of the gas at the output of inlet tube 32 towards the patient 60. Since the agent from the agent vaporizer 22 is carried in the fresh gas flow stream in the inlet tube 32 of the breathing circuit 14, a change in the fresh gas displacement from the gas flow controller 16 also changes the rate of agent displaced into the breathing circuit 14. Furthermore, the change in gas flow rate rapidly affects the inspired agent concentration as compared to a change in the vaporizer concentration setting at the agent vaporizer 22. By merely changing the vaporizer concentration setting in the agent vaporizer 22, there is a significant time delay before that change will reach the patient 60. This transport delay depends on the fresh gas flow rates and the gas mixing rates in the pipeline, and therefore has been unacceptable.

In order to achieve desirable control performance in the concentration priority mode, it is necessary that the gas and agent mixture entering the inlet tube 32 of the breathing circuit 14 be accurately measured or predicted. In this regard, the fresh gas supply 12 can accurately meter the exact amount of gases entering the breathing circuit 14, and if the gas and agent compositions entering the inlet tube 32 vary slowing and flow rates are low, acceptable control performance can readily be achieved. The gas and agent volume error, which can be caused by measurement or prediction inaccuracies, can then be offset by throttling the fresh gas flow in the gas flow controller 16. In a preferred embodiment, to minimize hardware costs and increase system reliability, a system with a slowly changing fresh gas composition combined with a prediction of the gas composition in the fresh gas line was found to function desirably.

Referring again to FIG. 2, central processor 20 is shown in a functional block diagram form with indications for signal flow. Processor 20 receives signals from the sensors 42 on data bus 58 and outputs signals to the agent vaporizer 22 on data bus 24 and to the gas flow controller 16 on data bus 18. The internal flow of the signals are diagramed to show feedforward control signals 70, feedback control signals 72, gain modifier signals 74, and data signals and measurements 76. Four basic modules are required for implementing the flow priority control. These are the user defined inspired agent concentration settings 78, minimum fresh gas flow target 80, vaporizer controller 82 and total fresh gas flow controller 84.

The user desired inspired agent concentration setting 78 operates in conjunction with the user interface 64, FIG. 1, to register user desired inspired gas concentration settings. The minimum fresh gas flow target 80, FIG. 2, functions for controlling oxygen and circuit volume control and provides the gas flow controller 84 with the minimum fresh gas flow (fgf) necessary for the other, nonagent, control and circuit needs. The vaporizer controller 82 and the total fresh gas flow controller 84 will be further described with reference to FIGS. 3 and 4. The user desired inspired agent concentration setting 78 and the minimum fresh gas flow target 80, together with the vaporizer controller 82 in the total fresh gas flow controller 84 are capable of operating the agent vaporizer and gas flow controller in the flow priority control.

In order to implement the concentration priority control, the following additional agent concentration computational modules 85 are required for estimating agent concentrations in the fresh gas line and the return line to achieve and support concentration priority control.

The fresh gas mixing characterization 86, determined a priori, together with the signal outputs 92 from the vaporizer controller 82 and the total fresh gas flow controller 84, are used to predict the instantaneous agent concentration transported through and delivered out the fresh gas pipeline in the fresh gas agent concentration delay estimator 88. In this manner, system behaviors that affect transport delays and mixing in the fresh gas line at various total fresh gas flow rates are captured a priori and are used in the prediction. Such prediction of the concentration output allows the control algorithm to look ahead and anticipate the quantity of anesthetic agent in the pipeline needed to achieve the set inspired concentration. By predicting the gas concentration in the pipeline, transport delays in controlling the anesthetic delivery are virtually eliminated because the system will know the amount of gas and agent that can be immediately delivered into the inspiratory section 34 of the breathing circuit 14, FIG. 1.

The amount of gas and agent recirculated from the carbon dioxide absorber 52, can then be estimated in the recirculated agent concentration estimator 90, FIG. 2. The recirculated agent concentration estimator 90 receives input from the fresh gas concentration delay estimator 88, the values of the sensors 42, that include agent concentration and minute volume, and the previous value for the total fresh gas flow controller 84. It is noted that the previous value for the total fresh gas flow controller signal is not shown schematically in the drawings to the recirculated agent concentration estimator 90 because it is assumed to be available to all modules in the system. The derived estimate from estimator 90 is then used in the total fresh gas flow controller 84 to compute the appropriate control value for the gas mixer. The recirculated agent concentration estimator is computed as follows:

$$Recirculated\_Agent\_Conc = \qquad [1]$$
$$(Minute\_Volume * Measured\_insp\_conc -$$
$$Current\_fgf * Fresh\_gas\_agent\_conc\_est) /$$
$$(Minute\_Volume - Current\_fgf)$$

The "Minute_Volume" and "Measured_insp_conc" are the values received from sensors 42, for the minute volume and the measured inspiratory agent concentration, respectively. The "Current_fgf" is the current fresh gas flow rate and the "Fresh_gas_agent_conc_est" is the estimate from the fresh gas agent concentration delay estimator 88.

Figure 3:
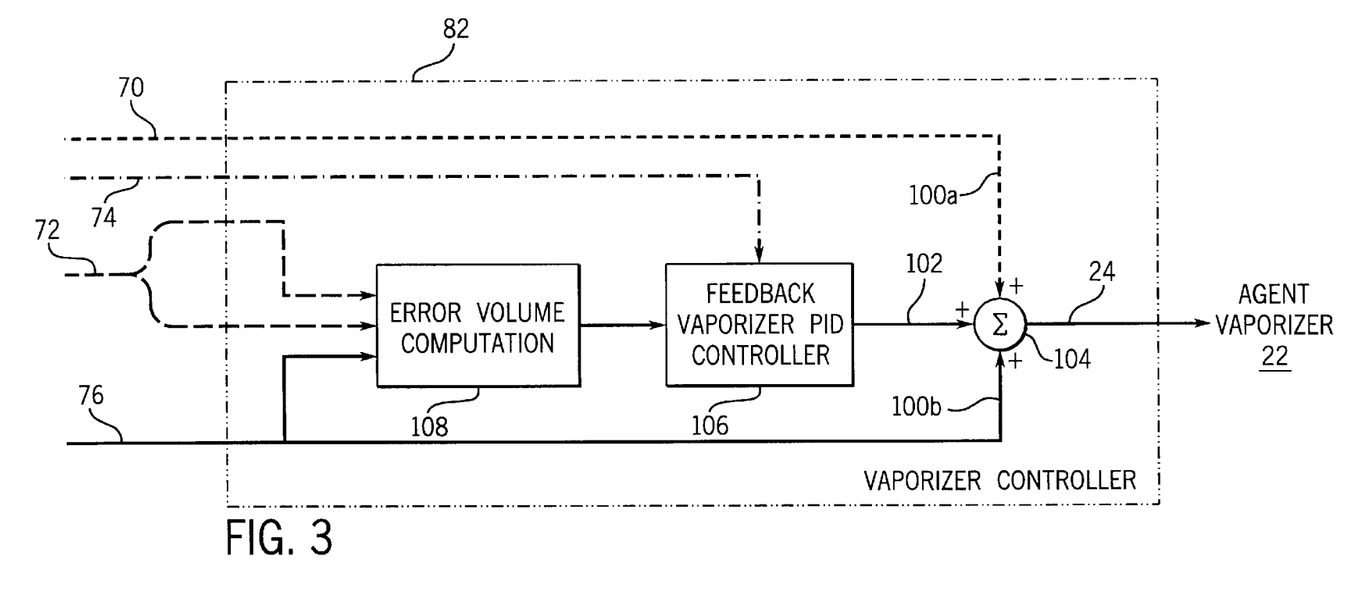
FIG. 3 is a functional block diagram of a portion of FIG. 2.

FIG. 3 shows a detailed view of the vaporizer controller 82 in functional block diagram form. The output on bus 24 of the vaporizer controller 82 (Vaporizer_conc) commands the delivery of the vaporizer 22, FIG. 1. There are two main components that contribute to the magnitude of the vaporizer output, a forced component 102 and a free component 100. The forced component 102 consists of a classical feedback Proportional Integral Derivative controller. The free component 100 consists of the output from the feedforward loading and flow reduction computation block 98, together with the user desired agent concentration signal 100b. The forced component 102 is a function of the agent concentration error while the free component 100 is set to cause the total fresh gas controller feedforward term to decrease the fresh gas flow. That is, as more agent comes out the fresh gas line, the flow controller will have to lower the flow to maintain the agent volume delivered. The forced component 102 is from hereinafter referred to as the vaporizer feedback component 102 and the free component is from hereinafter referred to as the vaporizer feedforward component 100. For a detailed explanation of the free/forced controller concept, reference is made to Advances in Model-Based Predictive Control by D. W. Clarke, as published by Oxford University Press, 1994.

Two components then that contribute to the magnitude of the vaporizer output, are the vaporizer feedforward 100 and the vaporizer feedback 102, $f_{vap,feedforward}(\ )$ and $f_{vap,feedback}(\ )$, respectively. The components 100 and 102 are combined at summer 104 as follows:

$$Vaporizer\_conc = f_{vap,\ feedforward}(K_{vap,\ FF}, F_{vap,\ Feedforward-loading}) + \qquad [2]$$
$$f_{vap,\ feedback}(K_{vap,\ FB}, F_{vap,PID})$$

where $F_{vap,\ Feedforward-loading}$ is the output from the feedforward loading and gain reduction computation block, and the $F_{vap,PID}$ is a negative feedback control function, each as will be further discuss below. The $F_{vap,PID}$ component responds to an agent concentration error and adjusts the vaporizer concentration delivery to minimize the agent concentration error. The agent concentration error is the difference between the outputs of the user desired inspired agent concentration to the agent circuit sensor 42 measurement. That is:

$$Agent\_concentration\_error = \qquad [3]$$
$$Set\_inspired\_conc - Measured\_insp\_conc.$$

A commonly used negative feedback control method is the Proportional-Integral-Derivative control (PID) algorithm, an example of which is described in Digital Control System Analysis and Design, Charles L. Phillips/H. Troy Nagle, Jr., Prentice-Hall, Inc. Page 254, PID Controllers. This negative feedback controlled method is implemented in the feedback vaporizer PID controller 106, FIG. 3. The contributions of the feedforward 100 and the feedback 102 components are governed by the normalized vaporizer control gains $K_{vap,FF}$ and $K_{vap,FB}$. The gain magnitudes are computed by the control priority gain modifier computation block 96, FIG. 2, as will be described. In this manner, the delivery system modifies the sensitivity of the vaporizer to minimize the agent concentration error. A large $K_{vap,FF}$ causes the vaporizer to act independently from the agent concentration error and a large $K_{vap,FB}$ causes the vaporizer to react quickly to a large concentration error.

By design of the flow priority mode, the gas flow controller typically operates at high flow rates. The flow rate is fixed or changes slowly as compared to the transport delay through the fresh gas flow path. The vaporizer controller 82, FIG. 3, is called upon to quickly minimize the agent concentration error using a negative feedback control of the vaporizer concentration. As previously described, this is accomplished by setting the gains $K_{vap,FF}$ low and $K_{vap,FB}$ high, as demonstrated in FIG. 10, which shows the normalized vaporizer controller gain schedules as will be described later.

In the concentration priority mode, the dominant contributor to the vaporizer concentration setting is the feedforward component 100. The feedback component 102 is made insensitive to the agent concentration error. To accomplish this effect, the gain modifier block 96, FIG. 2, effectively sets $K_{vap,FF}$ large and $K_{vap,FB}$ small. The feedforward loading and flow reduction computation block 98, sets the vaporizer delivery concentration, as will be more completely described later.

Figure 4:
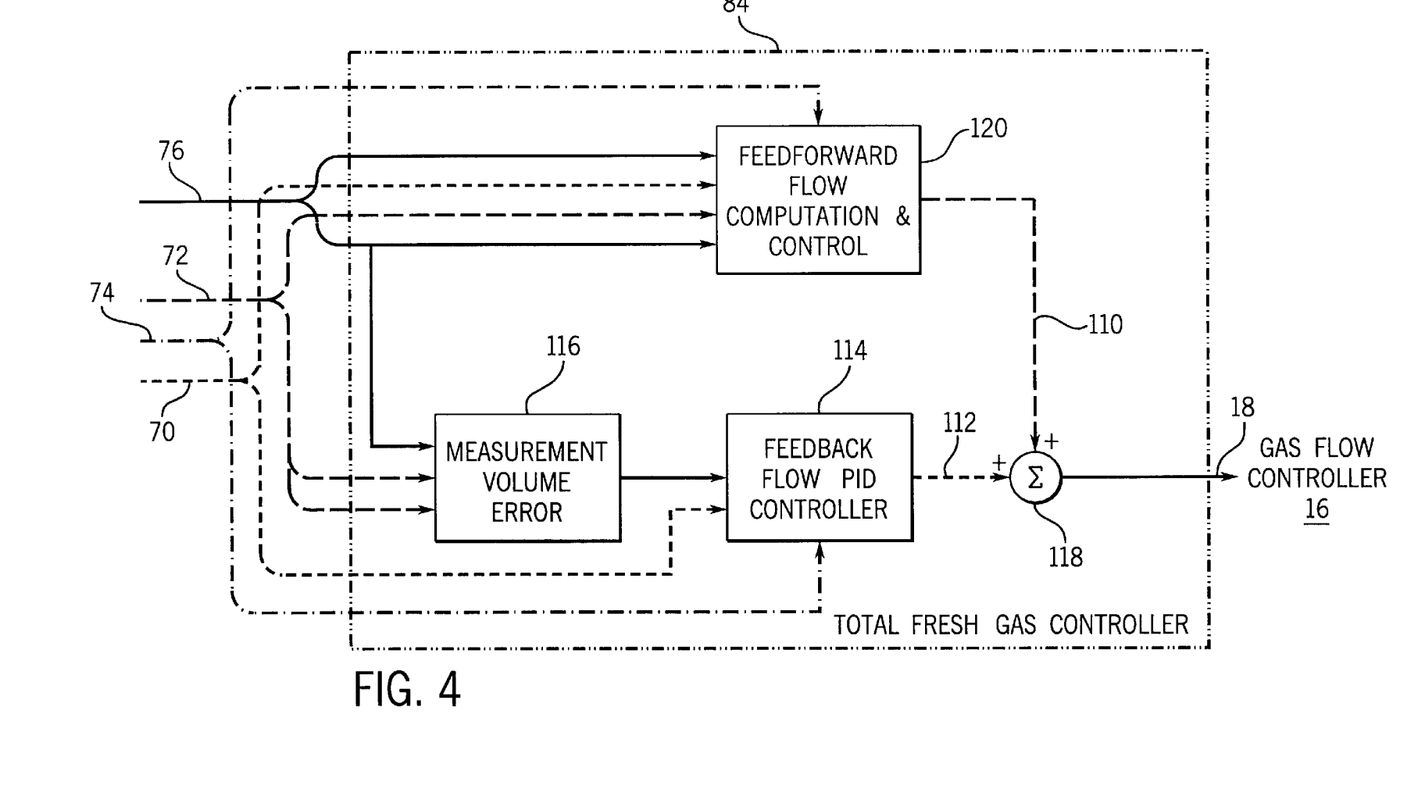
FIG. 4 is a functional block diagram of a portion of FIG. 2.

Referring to FIG. 4, the output of the total fresh gas flow controller 84 commands the total flow delivery to the gas flow controller 18. There are two components that contribute to the computation of the total fresh gas flow, a flow feedforward component 110 and a flow feedback component 112 (i.e, $f_{flow,\ feedforward}(\ )$ and $f_{flow,\ feedback}(\ )$, respectively). The components are combined in summer 118 as follows:

$$Total\_fresh\_gas\_flow = f_{flow, feedforward}(K_{flow, feedforward-loading}) + \quad [4]$$
$$f_{flow, feedback}(K_{flow, FB}, F_{flow, PID})$$

where $F_{flow, Feedforward-loading}$ is the output of the feedforward loading and flow reduction computation block 98, FIG. 2. $F_{flow,PID}$ is a negative feedback control function that operates on the gas flow controller to minimize the agent concentration error. Again, a commonly used negative feedback control method is the Proportional-Integral-Derivative algorithm and is implemented in the feedback flow PID controller 114. The contributions of the flow feedforward 110 and the flow feedback 112 components are governed by the normalized total fresh gas flow control gains, $K_{flow,FF}$ and $K_{flow, FB}$. The gain magnitudes are computed by the control priority gain modifier computation block 96, FIG. 2. In this manner, the delivery system alters the sensitivity of the gas flow controller to minimize the agent concentration error. A large $K_{flow,FF}$ causes the gas flow controller to act independently of the agent concentration error while a large $K_{flow,FB}$ causes the gas flow controller to react quickly.

By design of the flow priority mode, the dominant contributor to the total fresh gas flow controller 84 is the flow feedforward component. The flow feedforward loading and flow reduction computation block 98 sets the $F_{flow,\ Feedforward\text{-}loading}$. The $F_{flow,Feedforward\text{-}loading}$ is usually set high and forces the gas flow controller to deliver at high flow rates. Furthermore, $K_{flow,FF}$ is set high while $K_{flow,FB}$ is set low. This allows the total_fresh_gas_flow to be set independently of the agent concentration error. As previously described, the vaporizer controller 82 is called upon to quickly minimize the agent concentration error using an active negative feedback control 106 to the vaporizer concentration delivery.

In concentration priority mode the feedforward loading with flow reduction computation block 120 adjusts the flow to provide agent based on anticipated need as follows:

$$F_{flow,\ Feedforward-loading} = (1.0 - K_{ffl}) * Prev\_F_{flow,\ Feedforward-loading} + K_{ffl} * Minute\_Volume * (Set\_inspired\_conc - Recirculated\_agent\_conc\_est) / Delayed\_agent\_conc \quad [5]$$

where $K_{ffl}$ is a constant gain typically 0.1 Therefore, as the difference between the set inspired concentration and the recirculated agent concentration estimate is minimized, the $F_{flow,Feedforward\text{-}loading}$ component of the total fresh gas flow is reduced.

In the concentration priority mode, the total fresh gas flow controller 84 is called upon to quickly minimize the agent concentration error using an active negative feedback control 114 of the gas flow controller. The flow feedback component, $f_{flow,feedback}(\ )$ dominates when $K_{flow,FF}$ is set low or to zero while $K_{flow,FB}$ is set high. The negative feedback is computed in a few steps. The total fresh gas flow controller 84, FIG. 4, first computes the agent volume error 116, which is the quantity of agent needed to bring the measured concentration to the desired setting. The following equation computes the agent volume error 116 given the agent concentration error from Equation [3] and the minute volume from the sensors:

$$Agent\_volume\_error = \sum_{breath} \{Agent\_concentration\_error * Minute\_volume\} \quad [6]$$

where $\Sigma_{breath}$ is the summation over a breath period. The expected mean agent concentration, Mean_fg-conc, that leaves the fresh gas pipeline and is available to be added to the breathing circuit in the next breath period and is given by:

$$Mean\_fg\_conc = \sum_{breath} \{Fresh\_gas\_agent\_conc\_est * Current\_fgf\} \Big/ \sum_{breath} \{Current\_fgf\} \quad [7]$$

where Fresh_gas_agent_conc_est is the computed output of the fresh gas agent concentration delay estimator block 88, FIG. 2, that predicts the agent concentration in the fresh gas pipeline, and Current_fgf is the current total fresh gas flow rate. This equation assumes that the fresh gas agent concentration is fixed or at least slowly changing as compared to the rate of change of the agent volume error. This assumption is generally valid because of the design of the concentration priority mode, where the vaporizer concentration is fixed or adjusted slowly and independently of the agent concentration error.

As mentioned earlier, changes in the total fresh gas flow rate alter the quantity of agent delivered to the patient from the fresh gas pipeline. Consequently, the agent concentration error can be indirectly but quickly minimized by changing fresh gas flow. The amount of the flow change, Fgf_change, is obtained using the following equation:

$$Fgf\_change = Agent\_volume\_error / Mean\_fg\_conc \quad [8]$$

The Fgf_change can be formulated as a negative feedback control loop. Again, a commonly used control method is the Proportional-Integral-Derivative algorithm.

The following detailed description of the control priority section 93, which includes the control priority selector and flow reduction logic/profiler 94, the control priority gain modifier computation 96, and the feedforward loading and flow reduction computation 98, are all additional control logic required to implement the concentration priority control.

The control priority selector and flow reduction logic/profiler 94 uses outputs from the user desired inspired agent concentration setting 78, the recirculated agent concentration estimator 90, the circuit agent sensor 42, and the total fresh gas flow controller 84, to switch, or select, the control priority modes. The output from the control priority selector 94 signals the control priority gain modifier 96 to update the feedforward and feedback weighting gains in the vaporizer controller 82 and the total fresh gas flow controller 84. Block 94 also determines the direction of, and the profiles that drive, the changes of the fresh gas flow rate. The profiles for the rate of flow change are stored in block 94. As will be shown, the profiles may be expressed in the rate of flow or in vaporizer changes. A simple schedule may be a linear reduction from the current flow value to the minimum flow threshold. The feedforward loading block 98 uses the flow profiles to compute the feedforward values $F_{vap,Feedforward\text{-}loading}$ and $F_{flow,\ Feedforward\text{-}loading}$.

The feedforward loading and flow reduction computation 98 will now be described. In the flow priority mode, a signal is sent to the feedforward loading and flow reduction computation block 98 to compute the appropriate total feedforward flow rates, $F_{flow\_Feedforward\text{-}loading}$ to be delivered by the gas flow controller. This computation sets a fresh gas flow rate that is sufficient for the vaporizer feedback control, $F_{vap,FB}$, to achieve the user desired inspired agent concentration setting. Inputs to block 98 include the current fresh gas flow rate, minute volume, recirculated agent concentration estimate set inspired concentration and the flow reduction profile.

Since a goal of the electronic anesthesia delivery system is to reduce the total drug usage, typically, lowering the total fresh gas flow will achieve this objective. In the flow priority mode, the optimal flow is achieved directly by progressively commanding lower total fresh gas flow rates. The total flow rate can then be lowered as long as there is sufficient fresh gas to replenish the breathing circuit volume, and to supply $O_2$ and agent to meet the inspired concentration setting. This minimum flow rate threshold is processed by the minimum fresh gas flow block 80. The rate of flow reduction is provided by the flow reduction logic/profiler block 94. As long as the flow rate exceeds the minimum flow threshold, the total fresh gas flow can be set independent of the control loop thereby virtually eliminating the agent concentration error.

In the concentration priority mode, a signal is sent to the feedforward loading and flow reduction computation block 98 to compute the appropriate vapor concentration to be delivered by the electronic vaporizer, $F_{vap,Feedforward\text{-}loading}$. The purpose of this computation is to ensure that there is sufficient quantity of agent in the fresh gas pipeline for the total fresh gas feedback control, $F_{flow,FB}$, in order to achieve the user desired inspired concentration setting 78 (Set_inspired_conc.).

Reduction of the total fresh gas flow rate in the concentration priority mode is indirect and is achieved by changing the vaporizer setting in the direction that forces the total fresh gas flow to be reduced in magnitude while maintaining the Set_inspired_conc. As an example, where the return gas is at a lower concentration than the set inspired agent concentration, an increase in the vaporizer delivery forces the fresh gas flow rate to decrease in order to maintain the same inspired agent concentration. To compute the rate of change of the vaporizer setting, the flow reduction computation block first computes the agent volume need to meet the Set_inspired_conc:

$$Agent\_volume\_need = \sum_{breath} \{Set\_inspired\_conc * Minute\_volume - \quad [9]$$
$$Recirculated\_agent\_conc\_est *$$
$$(Minute\_volume - Current\_fgf)\}$$

where Current_fgf is the current fresh gas flow rate and the Recirculated_agent_conc_est is the output of the recirculated agent concentration estimator 90. A target for the vaporizer setting (Target_vaporizer_setting) is the anticipated vaporizer setting that provides sufficient vapor concentration in the fresh gas line at the minimum fresh gas flow threshold (Minimum_fgf) to maintain the Set_inspired_conc. Mathematically:

$$Target\_vaporizer\_setting = Agent\_volume\_need / Minimum\_fgf \quad [10]$$

Physical constraint of the vaporizer further limits the Target_vaporizer_setting. The $F_{vap,Feedforward\_loading}$ is updated by interpolating between the current vaporizer setting and the Target_vaporizer_setting along the flow reduction profiles. In this case, the flow reduction profiles are expressed as a rate of change of the vaporizer concentration setting, and are stored and processed in the flow reduction logic/profiler block 94, then computed in the flow reduction computation block 98.

The control priority gain modifier computation 96 varies the feedforward and feedback control gains to the vaporizer controller 82 and the total fresh gas flow controller 84 ($K_{vap,FF}$, $K_{vap,FB}$, $K_{flow,FF}$, and $K_{flow,FB}$), and forces one controller to be very sensitive and the other very insensitive to the agent concentration error. The less active controller accounts for the actuation of the priority mode variable while the more active controller rapidly removes the agent concentration error.

The gain values may depend on the open-loop characteristics of the anesthesia system. For example, the vaporizer controller gain ($K_{vap,\ FB}$) varies with the total fresh gas flow rate as indicated in the normalized vaporizer control gain schedule plot of FIG. 10. Regardless of the priority mode, it is desirable that the less active controller retains some weak feedback control effort to provide the independent controller with a slow adaptation to actuator errors, such as vaporizer concentration or gas mixer delivery errors.

Typically, the flow priority control mode is activated at high flow rates, for example at flow rates greater than 4 L/Min, or greater than 70%. of minute volume, or when the flow is fixed. In this mode, the independent priority controlled variable is the total fresh gas flow rate and the dependent controlled variable is the vaporizer concentration setting. The total fresh gas flow rate is determined independently of the agent concentration error. The flow rate is set to rapidly achieve a new user set inspired concentration, or lowered when the agent concentration error is small and yet there is sufficient flow for the vaporizer controller 82 to maintain rapid feedback control. The vaporizer controller 82 is made very sensitive to the agent concentration error. Along with high fresh gas flow rates and small transport delay times, the anesthesia delivery system of the present invention rapidly tracks the user defined inspired concentration.

The concentration priority control mode is typically activated at low flow rates, for example, at flow rates less than 3 L/Min or less than 70% of minute volume. In this mode, the independent priority controlled variable is the vaporizer concentration setting and the dependent controlled variable is the fresh gas flow rate. The vaporizer delivery is adjusted independently of the inspired agent concentration error. The highest tolerable concentration is loaded. The loading takes into account rapid achievement of Set_inspired_conc at the lowest flow rate, or reduction of fresh gas flow rate after the inspired agent concentration is achieved, for example say within 10% of setting. The total fresh gas flow controller 84 is made very sensitive to the agent concentration error. Feedback control of the total fresh gas flow rate enables the anesthesia delivery system of the present invention to track the Set_inspired_conc without transport delays.

Control priority modes are changed in several clinical sittuations. Switching conditions are derived from the user setting, total fresh gas flow rates, agent concentration in the fresh gas pipeline, minute volume, and agent volume need.

Non-exhaustive examples of conditions that may switch the control priority from the concentration priority mode to the flow priority mode, include when the gas concentration in the fresh gas pipeline cannot adequately or quickly meet the user set concentration. For example, when:

the user commands a large concentration setting change at low flows;

the user commands concentration that switches between wash in and wash out of patient gases; or a large gas concentration disturbance is recirculated from the $CO_2$ absorber. Another example would be when the clinical demand to switch from a low to high fresh gas flow rate is desired, for example, during induction.

Examples of conditions desirable to switch from the flow priority mode to the concentration priority mode, include when there is a sluggish concentration control because of low flow operation. For example, when:

the fresh gas flow is sufficiently reduced from the start of the flow priority mode, or there is a clinical demand to switch from a high to low fresh gas flow rate.

Figure 5:
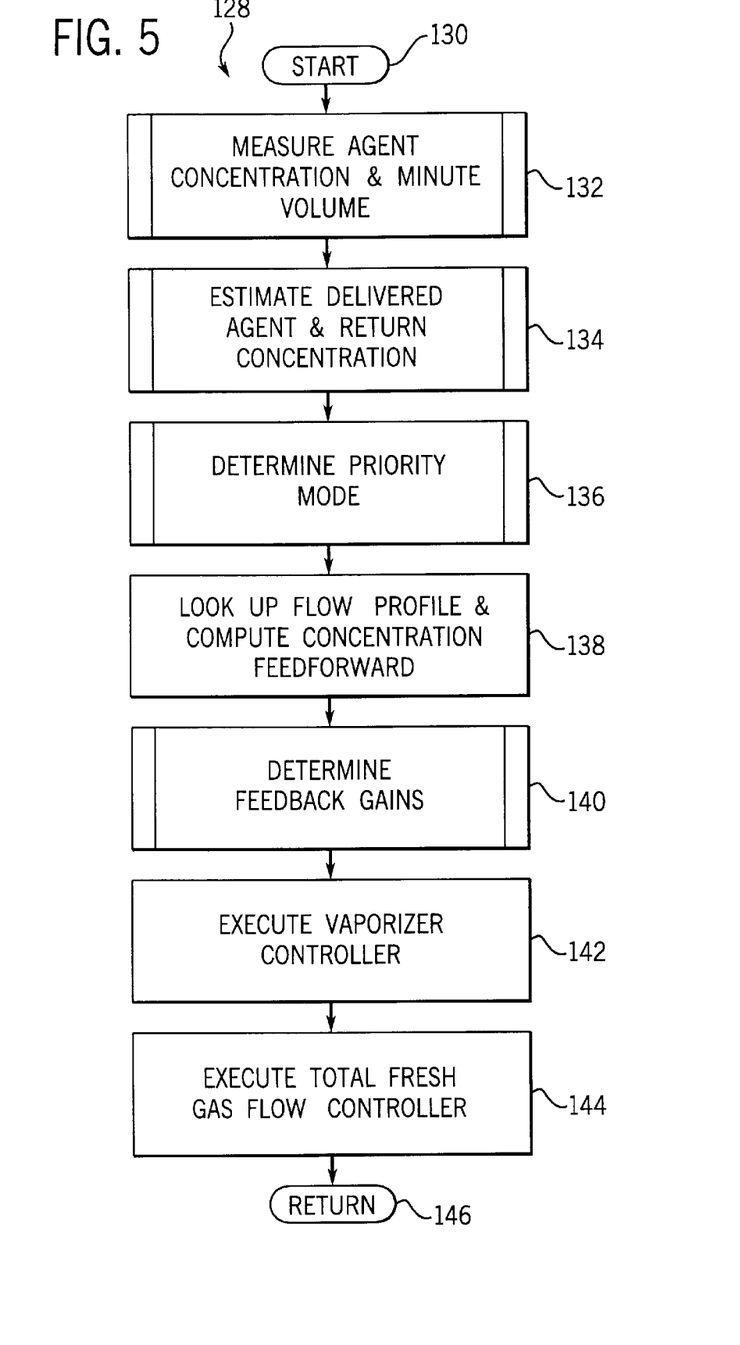
FIG. 5 is a flow chart of an anesthesia delivery system control according to the present invention.

Referring now to FIG. 5, the main algorithm 128 of the anesthesia delivery system control of the present invention is shown in flow chart form. After initialization 130, the inputs are updated at 132 which includes measuring the agent concentration and minute volumes as determined by the circuit agent sensor and the minute volume sensor. Additionally, the user inspired agent concentration setting and the minimum fresh gas target are acquired. Once the inputs are updated, the estimators are updated at 134, which includes estimating the delivered agent and the return concentration from the fresh gas agent delay estimator and the recirculated agent concentration estimator. Thereafter, the priority mode is determined at 136 via the control priority selector to compute the agent volume need, as accumulated over a breath cycle, to determine the difference between the set and the measured concentrations. Additionally, a determination is made as to whether the agent volume need can be maintained by the current control priority, and if not, the control priority is switched as necessary. Next, the flow profile is determined and the concentration feedforward is computed at 138 in the flow reduction logic/profiler to determine if the agent volume need can be maintained by the direction of flow changes, and the direction of flow changes is switched if necessary. If flow can be reduced, the flow reduction profile is computed. The concentration feedforward is determined in the feedforward loading and flow reduction computation to compute the independent feedforward value using the flow reduction profile provided by the flow reduction logic/profiler output. Thereafter, the feedback gains are determined at 140 by the control priority gain modifier to compute controller gains based on priority modes and fresh gas flow rates. Next, the vaporizer controller is executed at 142 and the controlled variables are updated. Lastly, the total fresh gas flow controller is executed at 144 and the system can return 146 to again update the inputs at 132.

Figures 6, 7, 8:
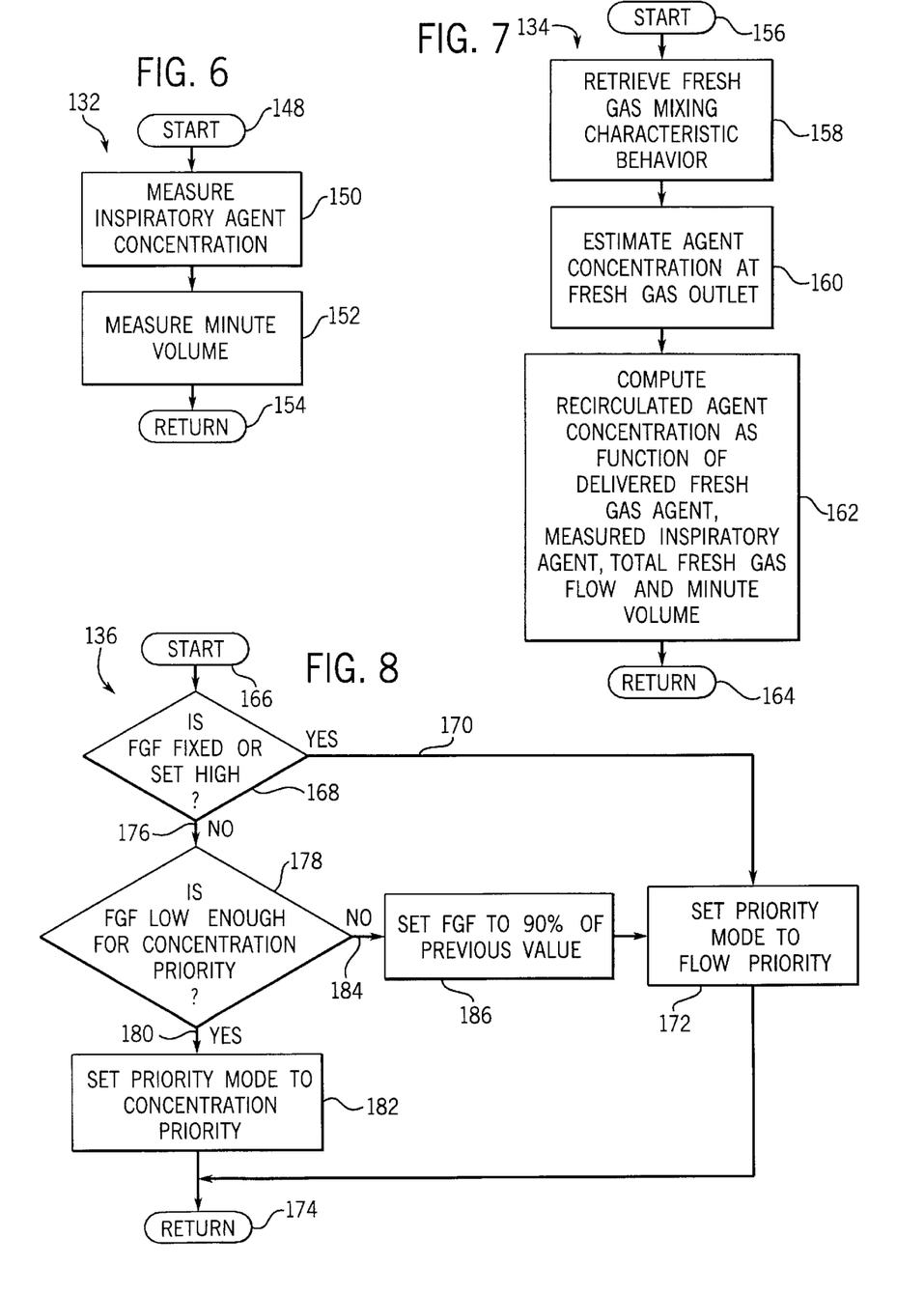
FIG. 6 is an expanded flow chart of a portion of FIG. 5.
FIG. 7 is an expanded flow chart of a portion of FIG. 5.
FIG. 8 is an expanded flow chart of a portion of FIG. 5.

FIG. 6 shows an expanded flow chart for updating the inputs 132. As previously described, after this subroutine is initiated at 148, the inspiratory agent concentration is measured at 150 and the minute volume is acquired at 152, at which time a subroutine returns 154 to the main algorithm.

FIG. 7 shows the estimator subroutine 134. Once initialized 156, the fresh gas mixing characteristic behavior is retrieved at 158 and the agent concentration at the fresh gas outlet is estimated at 160. The recirculated agent concentration as a function of the delivered fresh gas agent can then be computed at 162, along with measuring the inspiratory agent, the total fresh gas flow, and the minute volume. Once the estimations are acquired, subroutine 134 returns 164 to the main algorithm 128.

The next subroutine is to determine the priority mode 136 as shown in FIG. 8. Once initialized 166, a determination is made as to whether the fresh gas flow is fixed or set high at 168. If either is true 170 the priority mode is set to flow priority at 172 and the subroutine is allowed to exit and return 174 to the main algorithm 128. If, on the other hand, the fresh gas flow is neither fixed nor set high 176, the fresh gas flow is checked to see if it is low enough for entry into the concentration priority at 178, and if so, 180, the priority mode is set to concentration priority 182 and the priority mode determination subroutine 136 returns 174 to the main algorithm 128. However, if the fresh gas flow is neither fixed nor set high 176, but is not low enough to enter the concentration priority mode 184, the fresh gas flow is set to 90% of the previous value at 186 and the priority mode is set to flow priority control mode 172, whereafter the priority mode determination subroutine 136 is allowed to return 174 to the main algorithm 128.

Figure 9:
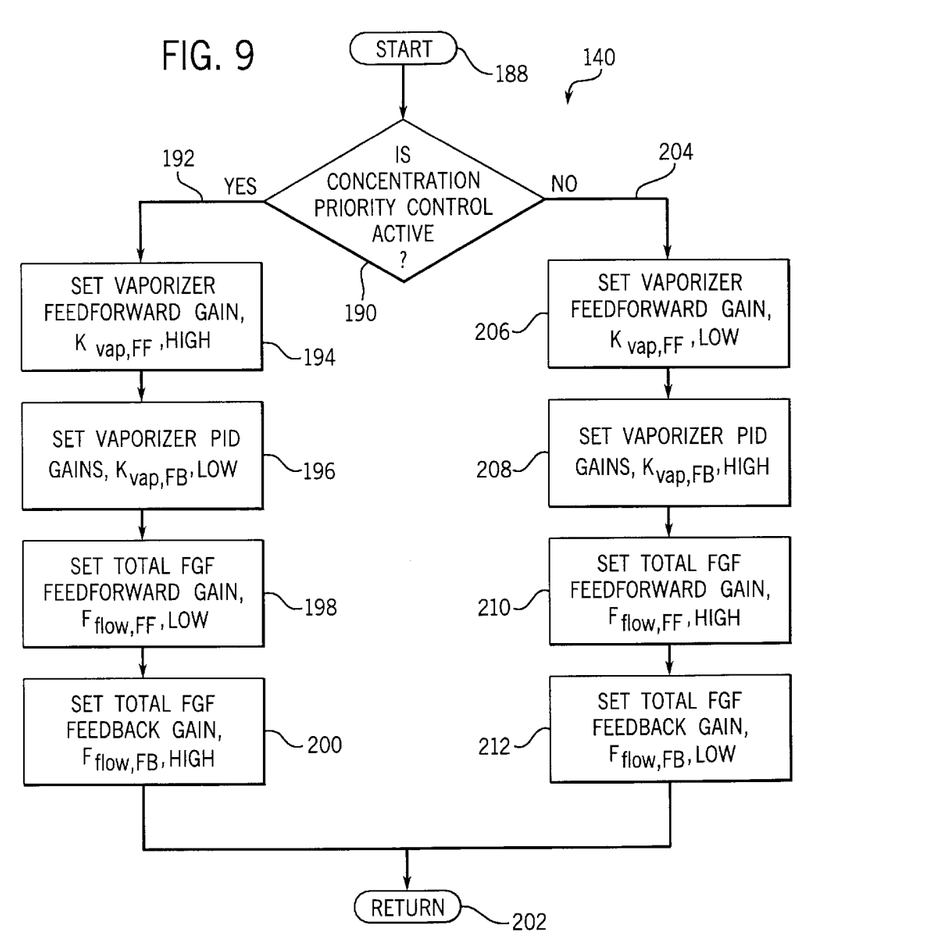
FIG. 9 is an expanded flow chart of a portion of FIG. 5.

Once back at the main subroutine 128, after the look up flow profile and compute concentration feedforward routine 138 is complete, the feedback gains determination subroutine 140 is initiated at 188 as shown in FIG. 9. If concentration priority control is activated 190, 192, the vaporizer feedforward gain is set high at 194 and the gain for the vaporizer PID is set low at 196. The total fresh gas flow feedforward gain is set low at 198 and the total fresh gas feedback gain is set high at 200, after which the feedback gains subroutine is complete and returns 202 to the main algorithm 128. However, if after initiating the feedback gains subroutine 140, the concentration priority control is not active 190, 204, then the vaporizer feedforward gain is set low at 206, the vaporizer PID gain is set high at 208, the total fresh gas flow feedforward gain is set high at 210, and the total fresh flow feedback gain is set low at 212, after which the subroutine returns 202 to the main algorithm 128 to complete the execution of the vaporizer controller 142 and the total fresh gas flow controller 144.

Figure 10:
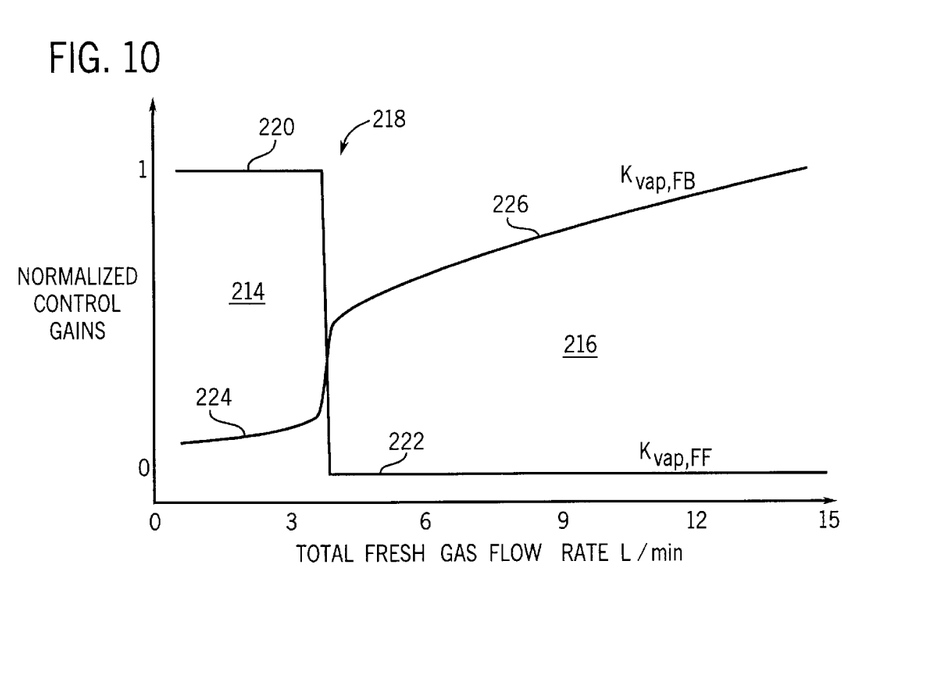
FIG. 10 is a graph showing normalized feedforward and feedback vaporizer control gains in various control priority modes.
Figure 11:
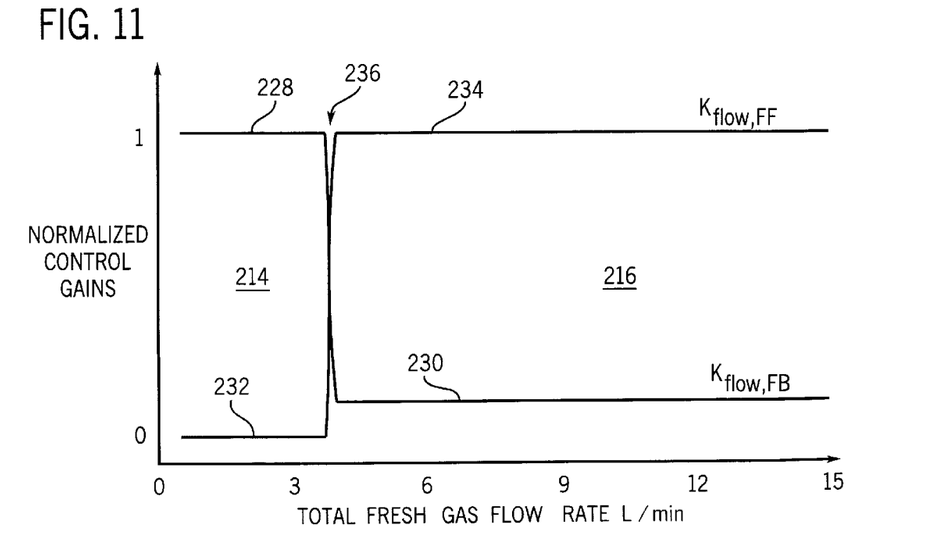
FIG. 11 is a graph showing normalized feedforward and feedback fresh gas control gains in various control priority modes.

FIGS. 10 and 11 show exemplary graphs for setting the control gains. The determination of the gains has been previously described, however, FIGS. 10 and 11 provide a quantitative schedules for the gains. The data in each of the graphs is determined a priori. FIG. 10 is a normalized feedforward and feedback vaporizer control gains schedule for operating in various control priority modes. The feedforward gain schedule, $K_{vap,FF}$ is shown high 220 where the target total fresh gas flow rate is low, and low 222 for target total fresh gas flow rates above approximately 4 L/Min. For the vaporizer control feedback gain, $K_{vap,FB}$, when in the concentration priority mode 214, the feedback gain is low 224, and increases across the mode transition 218 and then increases less drastically 226 through the flow priority mode 216.

FIG. 11 shows the normalized feedforward and feedback gains for the total fresh gas flow control operating in various control priority modes. The feedback gain, $K_{flow,FB}$ is high 228 while in the concentration priority mode 214 for low fresh gas flow rates and low 230 for fresh gas flow rates above approximately 4 L/Min. The feedforward gain, $K_{flow,FF}$, is conversely low 232 in the concentration priority mode 214 and high 234 in the flow priority mode 216. As shown, each of the gains adjust dramatically during a mode transition 236, at approximately 4 L/Min.

It is contemplated that the control, although preferably disclosed in terms of a programmed micro-processor, can be alternatively implemented with discrete control logic. The present invention has been described in terms of the preferred embodiment, and it is recognized that equivalents, alternatives, and modifications, aside from those expressly stated, are possible and within the scope of the appending claims.

We claim:

1. An anesthetic agent delivery system for delivering a desired dose of anesthetic agent to a patient comprising:

an anesthetic agent supply having a controller for controlling the amount of anesthetic agent provided by the supply;

a gas supply for providing respiratory gas, said gas supply being in fluid communication with said anesthetic agent supply to receive the anesthetic agent from said anesthetic agent supply to form fresh gas, said gas supply having a gas flow controller for controlling the fresh gas flow rate;

a breathing circuit containing and recirculating breathing gas for the patient, said breathing circuit having a supply end and a patient end that is in communication with the patient, said breathing circuit being formed such that a gas volume displacement at the supply end will cause a rapid, corresponding volume displacement at the patient end, said supply end being in communication with the gas supply and the anesthetic agent supply to receive fresh gas into the breathing circuit, the breathing circuit providing a minute volume of breathing gas to the patient;

a sensor connected in the breathing circuit to provide a signal indicative of the anesthetic agent concentration delivered to the patient; and a system control connected to the gas flow controller and anesthetic agent supply controller, said system control receiving the signal from said sensor for forming an anesthetic agent concentration error signal indicative of the difference between desired and delivered patient anesthetic agent concentrations, the system control having a plurality of control paths to control the anesthetic agent concentration delivered to the patient, said system control employing, when the fresh gas flow rate is less than or equal to the minute volume, a first control path comprising a feedforward control loop for said anesthetic agent supply for establishing the amount of anesthetic agent provided in the fresh gas by said anesthetic agent supply, and employing a second control path comprising a feedback control loop between said anesthetic agent concentration error signal and said gas flow controller to rapidly and incrementally change the fresh gas flow rate in a manner to rapidly minimize an error between desired and delivered patient anesthetic agent concentrations, said system control having switching means responsive to the fresh gas flow rate to switch from said first and second control paths to third and fourth control paths when the fresh gas flow rate exceeds the minute volume, said third control path comprising a feedforward control loop which is coupled to said gas flow controller for establishing the flow rate of the fresh gas, and said fourth control path comprising a closed, feedback control loop between the anesthetic agent concentration error signal and said anesthetic agent supply controller to vary the amount of anesthetic agent provided by said anesthetic agent supply in the fresh gas in a manner to minimize the error between desired and delivered patient anesthetic agent concentrations.

2. The system of claim 1 wherein said switching means carries out the switching using weighted signal gains for said control paths.

3. The system of claim 1 wherein said feedback control loops contain a proportional-integral-derivative controller.

4. The system of claim 2 wherein said feedback control loops contain a proportional-integral-derivative controller.

5. The system of claim 1 further including means for establishing a magnitude for the concentration of anesthetic agent in the fresh gas received into the breathing circuit; means for establishing a magnitude for the concentration of anesthetic agent in the recirculating breathing gas in the breathing circuit; and means for changing the fresh gas flow rate in accordance with the established magnitudes to minimize the error between desired and delivered anesthetic agent concentrations.

6. The system of claim 5 wherein at least one of said magnitude establishing means is further defined as means for estimating the magnitude of the concentration of anesthetic agent.

7. The system of claim 6 wherein said means for establishing a magnitude for the concentration of anesthetic gas in the fresh gas further comprises means providing an indication of a fresh gas mixing characterization that is determined, a priori, based on the configuration of the anesthesia delivery system, and a fresh gas transport delay estimator to predict delay characteristics in the transport of the fresh gas to the breathing circuit.

8. The system of claim 6 wherein said means for establishing a magnitude for the concentration of anesthetic agent in the recirculating breathing gases further comprises a recirculating agent concentration estimator to estimate the amount of anesthetic agent recirculated in the breathing circuit.

9. The system of claim 1 wherein said switching means is flirter defined as switching to said third and fourth control loops when the fresh gas flow rate is about 4 L/Min or above.

10. The system of claim 9 wherein said switching means is further defined as switching back from said third and fourth control paths to said first and second control paths when the fresh gas flow rate decreases to about 3 L/Min or less.

11. The system of claim 1 further comprising a user interface connected to said system control to provide a user desired patient anesthetic agent concentration value.

12. The system of claim 1 wherein said user interface is further defined as providing a user desired minimum fresh gas flow rate value to cause said gas flow controller to provide a desired minimum fresh gas flow rate to the breathing circuit.

13. A method for delivering a desired dose of anesthetic agent to a patient comprising the steps of:

providing a controllable flow of respiratory gas;

providing a controllable amount of anesthetic agent;

mixing the respiratory gas and anesthetic agent to form fresh gas, the flow rate of which and the amount of anesthetic agent contained therein are controllable;

supplying a minute volume of breathing gas to the patient with a breathing circuit containing and recirculating the breathing gas, said breathing circuit being formed such that a gas volume displacement at a supply end will cause rapid, corresponding gas volume displacement at a patient end that is in communication with the patient:

supplying the fresh gas into the breathing circuit at the supply end;

sensing the anesthetic agent concentration delivered to the patient by the breathing circuit and providing an aesthetic agent concentration error signal indicative of the difference between desired and delivered patient anesthetic concentrations;

when the flow rate of the fresh gas into the breathing circuit is less than or equal to the minute volume, establishing the amount of anesthetic agent provided in the fresh gas and controlling the fresh gas flow rate responsive to the error signal to rapidly and incrementally change the fresh gas flow rate in a manner to rapidly minimize an error between desired and delivered patient concentrations; and when the flow rate of the fresh gas to the breathing circuit exceeds the minute volume, establishing the flow rate for the fresh gas and controlling the amount of anesthetic agent contained in the fresh gas responsive to the error signal in a manner to minimize an error between desired and delivered patient anesthetic agent concentrations.

14. The method of claim 13 further including the step of providing weighted signal gains to select control paths having desired characteristics that establish and control the amount anesthetic agent and fresh gas flow rate.

15. The method of claim 13 further including the step of carrying out proportional-integral-derivative control in closed, feedback control paths to control the amount of anesthetic agent and fresh gas flow rate.

16. The method of claim 14 further including the step of carrying out proportional-integral-derivative control in closed, feedback control paths to control the amount of anesthetic agent and fresh gas flow rate.

17. The method of claim 14 further defined as periodically ascertaining the fresh gas flow rate and updating the weighted signal gains provided to the control paths.

18. The method of claim 13 further including steps of establishing a magnitude for the concentration of anesthetic agent in the fresh gas received into the breathing circuit; establishing a magnitude for the concentration of anesthetic agent in the recirculating breathing gas in the breathing circuit; and changing the fresh gas flow rate in accordance with the established magnitudes to minimize the error between desired and delivered anesthetic agent concentrations.

19. The method of claim 18 wherein at least one of said magnitude establishing steps is further defined as estimating the magnitude of the concentration of anesthetic agent.

20. The method of claim 19 wherein the step of establishing the magnitude for the concentration of anesthetic gas in the fresh gas further comprises the step of providing an indication of a fresh gas mixing characterization that is determined, a priori, based on the configuration of the anesthesia delivery system, and the step of predicting delay characteristics in the transport of the fresh gas to the breathing circuit.

21. The method o f claim 19 wherein the step of establishing the magnitude for the concentration of anesthetic agent in the recirculating breathing gases further comprises estimating the amount of anesthetic agent recirculating in the breathing circuit.

22. The method of claim 13 wherein the method is further defined as switching from the operative mode described in the penultimate step to the operation mode described in the last step when the fresh gas flow rate is about 4 L/Min or above.

23. The method of claim 22 wherein the method is further defined as switching back from the mode of operation described in the last step to the mode of operation described in the penultimate step when the fresh gas flow rate decreases to about 3 L/Min or less.

24. The method of claim 13 further comprising the step of providing a user desired patient anesthetic agent concentration.

25. The method of claim 13 further comprising the steps of providing a user desired minimum fresh gas flow value rate and providing a desired minimum fresh gas flow rate to the breathing circuit.

\* \* \* \* \*